United States Patent [19]

Marchetti

[11] 4,020,082
[45] Apr. 26, 1977

[54] 2-AMINOMETHYL- AND 2-(2-AMINOETHYL)-SUBSTITUTED 4,5-DIPHENYLOXAZOLES

[76] Inventor: Enzo Marchetti, Via Casilina 125, Rome, Italy

[22] Filed: Aug. 5, 1975

[21] Appl. No.: 602,097

Related U.S. Application Data

[63] Continuation-in-part of Ser. No. 117,117, Feb. 19, 1971, abandoned.

[30] Foreign Application Priority Data

Feb. 21, 1970 Italy .................................. 20946/70

[52] U.S. Cl. ..................... 260/307 R; 260/247.5 E; 260/268 H; 260/293.67; 260/559 R; 260/559 A; 260/570.5 C; 424/248.4; 424/250; 424/267; 424/272
[51] Int. Cl.² ............. C07D 263/32; C07D 413/06
[58] Field of Search ............................... 260/307 R

[56] References Cited

OTHER PUBLICATIONS

Mattalia et al. - Farmaco, Ed. Sci. 1971, 26(6), 512–519.
Marchetti - C. A. 76, 46188q (1972) - Abstract of Ger. Offen. 2,108,437.

*Primary Examiner*—Donald G. Daus
*Assistant Examiner*—David E. Wheeler
*Attorney, Agent, or Firm*—Cameron, Kerkam, Sutton, Stowell & Stowell

[57] ABSTRACT

2-Aminomethyl- and 2-(2-aminoethyl)-substituted 4,5-diphenyloxazoles of the general formula

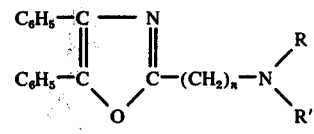

and salts thereof with non-toxic organic or inorganic acids having antiphlogistic, analgesic, anti-aggregant and local anaesthetic properties with low toxicity are provided, as well as processes for preparing them.

6 Claims, No Drawings

2-AMINOMETHYL- AND 2-(2-AMINOETHYL)-SUBSTITUTED 4,5-DIPHENYLOXAZOLES

RELATED APPLICATIONS

This is a continuation-in-part application of co-pending application Ser. No. 117,117, filed Feb. 19, 1971, now abandoned.

This invention relates to a series of 2-aminomethyl- and 2-(2-aminoethyl)-substituted 4,5-diphenyloxazoles of the general formula:

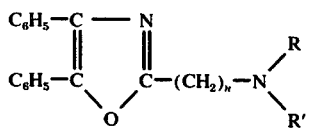

wherein $n$ is the integer 1 or 2 and R and R', which may be the same or different, represent hydrogen; alkyl of 1 to 4 carbon atoms; cycloalkyl having 5 to 6 ring members; phenylalkyl having 1 to 3 carbon atoms in the alkyl chain; hydroxyalkyl of 1 to 4 carbon atoms; acetoxyalkyl having 1 to 4 carbon atoms in the alkyl chain; dialkylaminoalkyl wherein the alkyl is of 1 to 4 carbon atoms; acyl of 1 to 4 carbon atoms; carbalkoxy having 1 to 4 carbon atoms in the alkyl chain; or form together with the nitrogen atom a heterocyclic structure of 5 to 6 ring members which can also comprise other hetero atoms or groups, such as O, NH, N—CH$_3$;

and to salts thereof with non-toxic organic or inorganic acids.

Preferably, in the general formula (I) the group

represents:

NH$_2$, NHCOCH$_3$, NHCOOC$_2$H$_5$, NHCH$_3$, N(COCH$_3$)CH$_3$, N(COOC$_2$H$_5$)CH$_3$, NHC$_2$H$_5$, NHCH$_2$CH$_2$OH, NHCH$_2$CH$_2$N(CH$_3$)$_2$, NHCH$_2$CH$_2$N(C$_2$H$_5$)$_2$, NHCH$_2$CH$_2$CH$_3$, NHCH(CH$_3$)$_2$, NHCH$_2$CH$_2$CH$_2$CH$_3$,

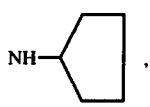, 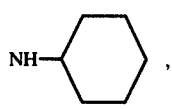,

NHCH$_2$CH$_2$C$_6$H$_5$, N(CH$_3$)$_2$, N(C$_2$H$_5$)$_2$,
N(CH$_2$CH$_2$OH)$_2$, N(CH$_2$CH$_2$OCOCH$_3$)$_2$,
N(CH$_2$CHOHCH$_3$)$_2$,

, ,

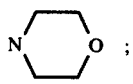; 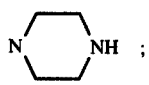;

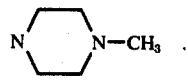

As results from tests carried out on experimental animals (mice, rats, guinea pigs, rabbits), the new compounds of this invention have anti-phlogistic, analgesic, anti-aggregant and local anaesthetic properties with a low toxicity.

This invention relates also to processes for preparing the compounds of the general formula (I).

The compounds of the general formula (I) wherein R and R' are as defined above (except when R and R' represent acyl or carbalkoxy) can be prepared by reacting a compound of the general formula (V):

wherein R and R' are as defined above (with the above restriction) with a 2-haloalkyl-4,5-diphenyloxazole (IV) which can be prepared in turn by acylating α-phenyl-α-aminoacetophenone (II) with a haloacid chloride and cyclizing with POCl$_3$ the resulting α-phenyl-α-haloacylamino-acetophenone (III):

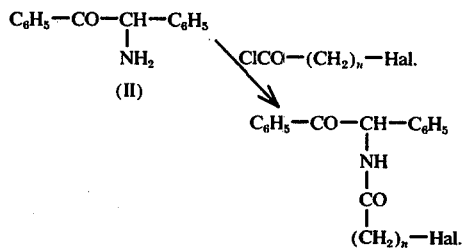

The above reactions are carried out in inert solvents such as benzene or toluene, at atmospheric pressure and at temperatures ranging from room temperature to the boiling point of the mixture. The reaction of the haloalkyloxazole (IV) with the compounds (V) is effected in the presence of an excess of the latter (at least at a ratio of 1:2) or by using equimolar amounts of the reagents in the presence of a base such as a tertiary amine as an acceptor of the hydrogen halide formed.

Alternatively, a haloacyl-derivative (III) can be reacted with an amino-derivative (V) and the resulting α-phenyl-α-aminoacylamino-acetophenone (VI) can be then cyclized with POCl₃ to give a 2-aminoalkyloxazole (I):

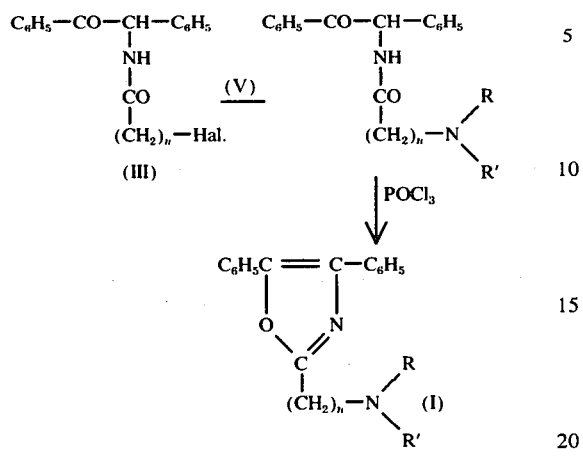

The same remarks as made about the preceding reaction scheme can be made about this scheme. In both schemes n is the integer 1 or 2; Hal. represents a halogen atom; preferably chlorine or bromine; and R and R' are as defined in the general formula (I), with the proviso that they do not represent acyl or carbalkoxy groups.

The compounds of the general formula (I) wherein R and R' can also represent acyl or carbalkoxy can be prepared by further acylating an aminoalkyloxazola prepared as described above wherein at least one of the R and R' represents hydrogen, with an acyl chloride or an alkyl chlorocarbonate, respectively, in an inert solvent such as benzene or toluene and in the presence of a base (e.g., a tertiary amine) as a hydrogen chloride acceptor.

The compounds of the general formula (I) can be reacted with physiologically tolerable inorganic or organic acids to give the corresponding slats.

The following illustrative and non-limitative Examples will illustrate more detailedly the new compounds of this invention and the methods for preparing them.

EXAMPLE 1 a. 2-chloromethyl-4,5-diphenyloxazole

A solution of 10 g. α-phenyl-α-chloroacetamidoacetophenone (prepared by acylating α-phenyl-α-aminoacetophenone with chloroacetyl chloride, m.p. 117°–119° C) and 8 ml. phosphorus oxychloride in 100 ml. anhydrous benzene was refluxed for 2 hours. The excess solvent was removed at 20 mm. pressure and the oily residue was dissolved in 80 ml. 70% ethanol. The resulting solution was cooled to 0° C to give 8.1 g. crystalline 2-chloromethyl-4,5-diphenyloxazole, m.p. 43°–45° C (yield 86%).

b. 2-methylaminomethyl-4,5-diphenyloxazole hydrochloride

A solution of 22 g. 2-chloromethyl-4,5-diphenyloxazole and 12.5 g methylamine in 100 ml. anhydrous benzene was heated at 120° C for 6 hours in a sealed tube. The reaction mixture was washed with water and the separated benzene phase was distilled at 20 mm. pressure. The oily residue was dissolved in 200 ml. anhydrous ether and a flow of gas hydrogen chloride was bubbled through the resulting solution. The 2-methylaminomethyl-4,5-diphenyloxazole hydrochloride was recrystallized from absolute ethanol: 16.5 g., m.p. 207°–208° C (yield 69%).

EXAMPLE 2

2-isopropylaminomethyl-4,5-diphenyloxazole hydrochloride

A mixture of 8 g. 2-chloromethyl-4,5-diphenyloxazole (prepared as described in Example 1a), 8g. isopropylamine and 50 ml. anhydrous benzene was kept in a stoppered flask for 48 hours at room temperature. The reaction mixture was washed with water and the separated benzene phase was distilled at 20 mm. pressure. The oily residue was dissolved in 100 ml. anhydrous ether and a flow of gas hydrogen chloride was bubbled through the resulting solution. The 2-isopropylaminomethyl-4,5-diphenyloxazole hydrochloride was recrystallized from absolute ethanol/anhydrous diethyl ether: 7.5 g., m.p. 197°–200° C (yield 76%).

EXAMPLE 3

2-n-butylaminomethyl-4,5-diphenyloxazole hydrochloride

A solution of 8 g. 2-chloromethyl-4,5-diphenyloxazole (prepared as described in Example 1a) and 6.6 g. n-butylamine in 100 ml. anhydrous benzene was refluxed for 4 hours. The reaction mixture was washed with water and the separated benzene phase was distilled at 20 mm. pressure. The oily residue was dissolved in 100 ml. anhydrous ether and a flow of gas hydrogen chloride was bubbled through the resulting solution. The 2-n-butylaminomethyl-4,5-diphenyloxazole hydrochloride was recrystallized from absolute ethanol/anhydrous diethyl ether: 7.4 g., m.p. 120°–123° C (yield 72%).

EXAMPLE 4

2-[bis(2-hydroxyethyl)-amino]-methyl-4,5-diphenyloxazole

A solution of 5.4 g. 2-chloromethyl-4,5-diphenyloxazole (prepared as described in Example 1a) and 6.3 g. diethanolamine in 50 ml. absolute ethanol was refluxed for 6 hours. The solvent was removed at 20 mm. pressure, the oily residue at 60° C was taken up with 100 ml. 60% ethanol by heating at 60–65° C and the water-alcohol solution was cooled to 0° C to give 5.7 g. crystalline 2-[bis(2-hydroxyethyl)-amino]-methyl-4,5-diphenyloxazole, m.p. 87°–88° C (yield 85%).

EXAMPLE 5

2-(4-methyl-1-piperazinyl)-methyl-4,5-diphenyloxazole

A mixture of 5.4 g. 2-chloromethyl-4,5-diphenyloxazole (prepared as described in Example 1a), 4 g. 4-methyl-piperazine and 50 ml. anhydrous benzene was refluxed for 4 hours. The reaction mixture was colled to 22°–25° C, washed with water and the separated benzene phase was distilled at 20 mm. pressure. The oily residue was suspended in 100 ml. ligroin (boiling range 40° to 60° C) to give 4.4 g. crystalline 2-(4-methyl-1-piperazinyl)-methyl-4,5-diphenyloxazole (yield 66%) which was then further purified by crystallization from anhydrous benzene/ligroin, m.p. 101°–102° C.

EXAMPLE 6

2-(8-dimethylaminoethyl)-aminomethyl-4,5-diphenyloxazole dihydrochloride

A solution of 8 g. 2-chloromethyl-4,5-diphenyloxazole (prepared as described in Example 1a) and 7.9 g. N,N-dimethyl ethylenediamine in 100 ml. anhydrous toluene was refluxed for 6 hours. The reaction mixture was washed with water and the separated toluene phase was evaporated at 5 mm. pressure. The oily residue was dissolved in 100 ml. anhydrous diethyl ether and a flow of gas hydrogen chloride was bubbled through the resulting solution. The precipitate 2-($\beta$-dimethylaminoethyl)-aminomethyl-4,5-diphenyloxazole dihydrochloride was then purified by crystallization from absolute ethanol/anhydrous diethyl ether: 5.5 g., m.p. 234°–238° C (yield 46%).

EXAMPLE 7

2-acetamidomethyl-4,5-diphenyloxazole 13 g. 2-aminomethyl-4,5-diphenyloxazole hydrochloride (prepared from 2-chloromethyl-4,5-diphenyloxazole and ammonia in accordance with the preceding Examples, m.p. 206°–207° C), 27.6 ml. triethylamine, 4.7 g. acetyl chloride and 300 ml. anhydrous benzene was refluxed for 4 hours. The reaction mixture was cooled to 22°–25° C, washed with water and then 5% sodium carbonate solution and the benzene phase was evaporated at 20 mm. pressure. The oily residue was dissolved in 80 ml. 70% ethanol and the water-cooled solution was cooled to 0° C to give 8.4 g. crystalline 2-acetamidomethyl-4,5-diphenyloxazole, m.p. 58°–60° C (yield 64%).

EXAMPLE 8

2-(N-methyl-N-carbethoxy)-aminomethyl-4,5-diphenyloxazole

A mixture of 10.5 g. 2-methylaminomethyl-4,5-diphenyloxazole hydrocloride (prepared as described in Example 1b), 14 ml. triethylamine and 4.8 g. ethyl ethylchlorocarbonate was dissolved in 200 ml. anhydrous benzene and refluxed for 5 hours. The reaction mixture was cooled to 22°–25° C, washed with water and the separated benzene phase was evaporated at 20 mm. pressure. The solid residue was dissolved in 150 ml. 70% ethanol by heating at 60°–70° C. The alcohol solution was then cooled to 0° C to give 9.5 g. crystalline 2-(N-methyl-N-carbethoxy)-aminomethyl-4,5-diphenyloxazole, m.p. 106°–107° C (yield 81%).

EXAMPLE 9 a. 2-($\beta$-bromoethyl)-4,5-diphenyloxazole

A solution of 50 g. $\alpha$-phenyl-$\alpha$-($\beta$-bromopropionamide)-acetophenone (prepared by acylating $\alpha$-phenyl-$\alpha$-aminoacetophenone with $\beta$-bromopropionyl chloride, m.p. 130°–133° C) and 32 ml. phosphorus oxychloride in 300 ml. benzene was refluxed for 3 hours. The excess solvent was removed at 20 mm. pressure and the oily residue was dissolved in 200 ml. 70% ethanol. The resulting solution was cooled to −10° C to give 25.4 g. crystalline 2-($\beta$-bromoethyl)-4,5-diphenyloxazole, m.p. 72°–74° C (yield 53%).

b. 2-($\beta$-morpholinoethyl)-4,5-diphenyloxazole hydrochloride

A mixture of 4.9 g. 2-($\beta$-bromoethyl)-4,5-diphenyloxazole and 3.9 g. morpholine in 40 ml. anhydrous benzene was maintained for 3 hours at 22°–25° C and for 1 hour at 80°–85° C. The reaction mixture was cooled to 22°–25° C, washed with water and the separated benzene phase was evaporated to dryness at 1 mm. residual pressure. The oily residue was dissolved in 100 ml. anhydrous diethyl ether and a flow of gas hydrogen chloride was bubbled through the resulting solution. The separated 2-($\beta$-morpholinoethyl)-4,5-diphenyloxazole hydrochloride (2.8 g.; yield 50%) was purified by crystallization from absolute ethanol/anhydrus ether, m.p. 200°–201° C.

EXAMPLE 10 a. $\alpha$-phenyl-$\alpha$-($\beta$-dimethylaminopropionamido)-acetophenone hydrochloride 10.4 g. $\alpha$-phenyl-$\alpha$-($\beta$-bromopropionamido)-acetophenone (prepared by acylating $\alpha$-phenyl-$\alpha$-amino-acetophenone with $\beta$-bromopropionyl chloride, m.p. 130°–133° C) and 13.5 g. dimethylamine in 150 ml. anhydrous benzene were heated at 100° C for 6 hours in a sealed tube. The reaction mixture was cooled to 22°–25° C, washed with water and the separated benzene phase was evaporated at 20 mm. pressure. The oily residue was dissolved in 100 ml. anhydrous ether and a flow of gas hydrogen chloride was bubbled through the resulting ethereal solution, whereby 8.7 g. $\alpha$-phenyl-$\alpha$-($\beta$-dimethylaminopropionamide)-acetophenone hydrochloride separated. The product was purified by crystallization from absolute ethanol, m.p. 173°–175° C (yield 83%).

b. 2-($\beta$-dimethylamino)-ethyl-4,5-diphenyloxazole hydrochloride 44 g. $\alpha$-phenyl-$\alpha$-($\beta$-dimethylaminopropionamido)-acetophenone, 20 ml. phosphorus axychloride and 50 ml. anhydrous benzene were refluxed for 3 hours. The mixture was cooled to 22°–25° C, washed with water and the organic phase was evaporated to dryness at 1 mm. pressure. The residue was dissolved in 100 ml. water, the aqueous solution was extracted with ether (the ethereal extracts were discarded) and then alkalinized with 10 ml. of a 10% sodium hydroxide aqueous solution. The separated oil was extracted with ether and a flow of gas hydrogen chloride was bubbled through the ethereal solution which had been previously dried over anhydrous sodium sulfate. The resulting 2-($\beta$-dimethylamino)-ethyl-4,5-diphenyl-oxazole hydrochloride (2.8 g.; yield 57%) was purified by crystallization from absolute ethanol/anhydrous ether, m.p. 182°–183° C.

In the following Table the compounds described in the preceding Examples and other compounds which can be obtained with similar procedures are listed together with the melting points of said compounds or salts thereof.

TABLE

| | |
|---|---|
| 1) 2-Aminomethyl-4,5-diphenyl-oxazole hydrochloride | m.p. 206°–207° C |
| 2) 2-Acetamidomethyl-4,5-diphenyl-oxazole | m.p. 58°–60° C |
| 3) 2-Carbethoxyaminomethyl-4,5-diphenyl-oxazole | m.p. 74°–75° C |

TABLE-continued 4) 2-Methylaminomethyl-4,5-diphenyl-oxazole hydrochloride — m.p. 207°–208° C
5) 2-(N-methyl-N-acetyl)-aminomethyl-4,5-diphenyl-oxazole — m.p. 101°–103° C
6) 2-(N-methyl-N-carbethoxy-)aminomethyl-4,5-diphenyl-oxazole — m.p. 106 –107° C
7) 2-Ethylaminomethyl-4,5-diphenyl-oxazole hydrochloride — m.p. 233°–235° C
8) 2-(2-hydroxymethyl)-aminomethyl-4,5-diphenyl-oxazole hydrochloride — m.p. 180°–182° C
9) 2-(2-dimethylaminoethyl)-aminomethyl-4,5-diphenyl-oxazole dihydrochloride — m.p. 234°–238° C
10) 2-(2-diethylaminoethyl)-aminomethyl-4,5-diphenyl-oxazole dihydrochloride — m.p. 206 –208° C
11) 2-n-Propylaminomethyl-4,5-diphenyl-oxazole hydrochloride — m.p. 175°–177° C
12) 2-Isopropylaminomethyl-4,5-diphenyl-oxazole hydrochloride — m.p. 197°–200° C
13) 2-n-Butylaminomethyl-4,5-diphenyl-oxazole hydrochloride — m.p. 120°–123° C
14) 2-Cyclopentylaminomethyl-4,5-diphenyl-oxazole hydrochloride — m.p. 144°–147° C
15) 2-Cyclohexylaminomethyl-4,5-diphenyl-oxazole hydrochloride — m.p. 198°–199° C
16) 2-(2-Phenylethyl)-aminomethyl-4,5-diphenyl-oxazole hydrochloride — m.p. 155°–157° C
17) 2-Dimethylaminomethyl-4,5-diphenyl-oxazole hydrochloride — m.p. 206°–209° C
18) 2-Diethylaminomethyl-4,5-diphenyl-oxazole hydrochloride — m.p. 155°–157° C
19) 2-(Bis-2-hydroxyethyl)-aminomethyl-4,5-diphenyl-oxazole — m.p. 87°–88° C
20) 2-(Bis-2-acetoxyethyl)aminomethyl-4,5-diphenyl-oxazole — m.p. 27°–30° C
21) 2-(Bis-2-hydroxypropyl)-aminomethyl-4,5-diphenyl-oxazole — (oil)
22) 2-Pyrrolidinomethyl-4,5-diphenyl-oxazole — m.p. 92°–94° C
23) 2-Piperidinomethyl-4,5-diphenyl-oxazole hydrochloride — m.p. 236°–237° C
24) 2-Morpholinomethyl-4,5-diphenyl-oxazole — m.p. 63°–65° C
25) 2-Piperazinomethyl-4,5-diphenyl-oxazole dihydrochloride — m.p. 225°–228° C
26) 2-(N'-methyl-N-piperazinyl)-methyl-4,5-diphenyl-oxazole — m.p. 101°–102° C
27) 2-(2-methylaminoethyl)-4,5-diphenyl-oxazole hydrochloride — m.p. 181 –182° C
28) 2-[2-(2-dimethylaminoethyl)-aminoethyl]-4,5-diphenyl-oxazole dihydrochloride — m.p. 155°–160° C
29) 2-(2-Isopropylaminoethyl)-4,5-diphenyl-oxazole hydrochloride — m.p. 204 –206° C
30) 2-(2-Cyclopentylaminoethyl)-4,5-diphenyl-oxazole hydrochloride — m.p. 213°–214° C
31) 2-(2-Dimethylaminoethyl)-4,5-diphenyl-oxazole hydrochloride — m.p. 182°–183° C
32) 2-(2-Pyrrolidinoethyl)-4,5-diphenyl-oxazole hydrochloride — m.p. 192°–193° C
33) 2-(2-Morpholinoethyl)-4,5-diphenyl-oxazole hydrochloride — m.p. 200°–201° C The following examples characterize the pharmacological properties of the compounds of the invention.

EXAMPLE 11

The anti-inflammatory and analgesic properties of the compounds of the invention were tested in groups of 10 Swiss mice which were observed for 5 days.

The anti-inflammatory activity was assayed by the carrageenin-induced paw oedema in rats (Winter et al, Proc. Soc. Exp., Biol., Vol. III, p. 544, 1962). The results are set forth in Table 1 and represent the relative potency of the tested compounds (as compared with phenylbutazone, the anti-inflammatory activity thereof at 100 mg/kg per os being assumed arbitrarily, to be equal to 1) after administration at a dose of 0.33 MLD per os.

The analgesic activity was tested according to the tail-pinching test (Bianchi et al, Brit. J. Pharmacol., Vol. 9, p. 280, 1954) and the hot plate test (Woolfe et al, J. Pharmacol. Exp. Ther., Vol. 80, p. 300, 1944). The results are also set forth in Table 1 and represent the relative potency of the tested compounds (as compared with aminopyrine, the analgesic activity thereof at 300 mg/kg os being assumed, arbitrarily, to be equal to 1) after administration at a dose of 0.33 MLD.

TABLE I

| R | n | Toxicity MLD (mice) mg/kg per os (a) | Anti-inflam. activity Test (relative potency) | Analgesic Activity Tail Pinching Test (Relative potency) | Hot Plate (Relative potency) |
|---|---|---|---|---|---|
| —NH$_2$ | 1 | 500 | 0.7 | 0.3 | 0.3 |
| —NHCOCH$_3$ | 1 | 1000 | 0.1 | 0.6 | 0.3 |
| —NH—COOC$_2$H$_5$ | 1 | 1000 | 0 | 0 | 0.3 |
| —NH—CH$_3$ | 1 | 500 | 0.9 | 1.2 | 0.9 |
| —N(CH$_3$)(COCH$_3$) | 1 | 900 | 0.25 | 0.8 | 0.8 |
| —N(CH$_3$)(COOC$_2$H$_5$) | 1 | 1000 | 0.5 | 0 | 0 |
| —NH—C$_2$H$_5$ | 1 | 700 | 0 | 0.5 | 0.1 |
| —NH—(CH$_2$)$_2$—C$_6$H$_5$ | 1 | 1000 | 0.3 | 0.2 | 0.1 |
| —NH—C$_3$H$_7$ | 1 | 800 | 0 | 0.1 | 0.6 |
| —NH—isoC$_3$H$_7$ | 1 | 900 | 0.5 | 0.5 | 0.2 |
| —NH—C$_4$H$_9$ | 1 | 500 | 0.3 | 0.5 | 0.1 |
| —NH—cyclopentyl | 1 | 700 | 0.3 | 0.5 | 0.3 |

Structure shown above table:

$$\begin{array}{c} C_6H_5 \\ | \\ C=C \\ / \quad \backslash \\ O \quad\quad N \\ \backslash \quad // \\ C-(CH_2)_n-R \end{array}$$

with two phenyl groups on the C=C carbons.

TABLE I-continued structure: 5-(diphenylmethylene)-2-substituted-4,5-dihydro-1,3-oxazole with C—(CH$_2$)$_n$—R

| R | n | Toxicity MLD (mice) mg/kg per os (a) | Anti-inflam. activity Test (relative potency) | Analgesic Activity Tail Pinching Test (Relative potency) | Hot Plate (Relative potency) |
|---|---|---|---|---|---|
| —NH—cyclohexyl | 1 | 400 | 0.5 | 0.1 | 0.5 |
| —N(CH$_3$)$_2$ | 1 | 500 | 0.2 | 0.8 | 0.7 |
| —N(C$_2$H$_5$)$_2$ | 1 | 500 | 1 | 3 | 3.8 |
| —NH(CH$_2$)$_2$N(CH$_3$)$_2$ | 1 | 300 | 0.7 | 0.1 | 0 |
| —NH(CH$_2$)$_2$N(C$_2$H$_5$)$_2$ | 1 | 300 | 0.1 | 0.2 | 0.1 |
| —NH—CH$_2$CH$_2$OH | 1 | 800 | 0.5 | 0.3 | 0.1 |
| —N(CH$_2$CH$_2$OH)$_2$ | 1 | 800 | 0.3 | 0.8 | 0.5 |
| —N(CH$_2$CH$_2$OCOCH$_3$)$_2$ | 1 | 700 | 0.4 | 0.9 | 0.6 |
| —N(CH$_2$CHOHCH$_3$)$_2$ | 1 | 400 | 0 | 0.3 | 0.6 |
| —N(pyrrolidinyl) | 1 | 1000 | 0.4 | 0.4 | 0.3 |
| —N(piperidinyl) | 1 | 800 | 0.25 | 0.8 | 0.8 |
| —N(morpholinyl) | 1 | 1000 | 0.8 | 1 | 1 |
| —N(piperazinyl)NH | 1 | 1000 | 0.5 | 0.8 | 0.1 |
| —N(N-methylpiperazinyl) | 1 | 600 | 0.3 | 0.9 | 0 |
| —NH—N(CH$_3$)$_2$ | 1 | 1000 | 0.5 | 0 | 0.15 |
| —NH—C(=NH)—NH$_2$ | 1 | 1000 | 0.4 | 0 | 0 |
| —NH—CH$_3$ | 2 | 500 | 0.9 | 1.1 | 0.9 |
| —NH—CH(CH$_3$)$_2$ | 2 | 700 | 0.8 | 0.4 | 0.5 |
| —NH—cyclopropyl | 2 | 800 | 0.9 | 0.5 | 0.4 |

TABLE I-continued

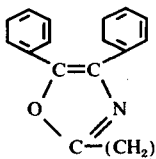

| R | n | Toxicity MLD (mice) mg/kg per os (a) | Anti-inflam. activity Test (relative potency) | Analgesic Activity Tail Pinching Test (Relative potency) | Hot Plate (Relative potency) |
|---|---|---|---|---|---|
| —NH—CH$_2$CH$_2$N(CH$_3$)(CH$_3$) | 2 | 1000 | 0.8 | 0.6 | 0.4 |
| —N(CH$_3$)(CH$_3$) | 2 | 500 | 0.5 | 0.5 | 0.2 |
| —N(morpholino) | 2 | 900 | 0.8 | 0.9 | 1 |
| —N(pyrrolidino) | 2 | 800 | 0.7 | 0.2 | 0.3 |

The compounds of the invention are also characterized by a strong inhibiting action on platelet aggregation often associated with a significant local anesthetic activity.

Although some non-steroid, anti-inflammatory drugs have been shown to be useful as anti-aggregating agents, it is known that these drugs are neither capable of inhibiting platelet aggregation in all of its forms, nor are they free from severe undesirable side effects.

As shown below, the compounds of this invention both inhibit ADP and collagen induced platelet aggregation. Inhibitory activity on platelet aggregation was determined in vitro on rabbit platelet-rich plasma at a constant temperature of 37° C, using the turbidometric method of Born described in Nature (London), 194, 927 (1962). Aggregation curves were read following the method described by O'Brien et al., Thromb, Diath. Haemorrhag. 16, 751 (1966).

Slope and maximum transmission were recorded and expressed as % change with respect to controls. In the case of collagen induced platelet aggregation, the delay time ("reaction time") in seconds from the addition of the aggregating agent to the inflection of the curve was also measured and expressed as % change as above. The results are summarized in Tables 2 and 3. Negative figures in slope and maximum transmission % changes indicate anti-aggregating activity; positive figures in delay time % changes indicate that the compound is effective in prolonging the "reaction time" in the collagen induced platelet aggregation test.

TABLE 2

ADP (5 μg/ml) INDUCED PLATELET AGGREGATION

| n | R | R' | Concentration μg/ml. | Max. transmission % change | Slope % Change |
|---|---|---|---|---|---|
| 1 | —CH$_2$CH$_2$OH | —CH$_2$CH$_2$OH | 100 | −22.3 | −12.1 |
|   |   |   | 50 | −16.6 | − 8.3 |
|   |   |   | 25 | − 5.1 | − 2.2 |
| 1 | —H | —CH$_2$CH$_2$N(C$_2$H$_5$)(C$_2$H$_5$) | 100 | −60.0 | −39.2 |
|   |   |   | 50 | −41.4 | −26.9 |
|   |   |   | 25 | − 7.8 | − 3.7 |
| 1 | —CH$_3$ | —COOC$_2$H$_5$ | 100 | −13.1 | −10.6 |
|   |   |   | 200 | −21.2 | −15.8 |
| 1 | —CH$_3$ | —CH$_3$ | 100 | −14.7 | −10.7 |
|   |   |   | 200 | −44.8 | −35.0 |
| 2 | —CH$_3$ | —CH$_3$ | 100 | −18.1 | −21.8 |
|   |   |   | 50 | − 6.0 | − 8.4 |
|   |   |   | 25 | − 3.2 | − 5.7 |

TABLE 3

COLLAGEN (40 μg/ml) INDUCED PLATELET AGGREGATION

| n | R | R' | Concen. μg/ml | Max. transmis. % change | Slope % Change | Reaction time - % change |
|---|---|---|---|---|---|---|
| 1 | CH$_2$CH$_2$OH | —CH$_2$CH$_2$OH | 5 | −60.2 | −58.8 | +74.0 |
|   |   |   | 2.5 | −51.3 | −52.2 | +45.9 |
|   |   |   | 1.25 | −22.2 | −25.5 | +10.3 |

TABLE 3-continued

COLLAGEN (40 μg/ml) INDUCED PLATELET AGGREGATION

| n | R | COMPOUND R' | Concen. μg/ml | Max. transmis. % change | Slope % Change | Reaction time - % change |
|---|---|---|---|---|---|---|
| 1 | —H | —CH$_2$CH$_2$N(C$_2$H$_5$)(C$_2$H$_5$) | 5 | −62.2 | −77.7 | +118.5 |
|   |   |   | 2.5 | −60.8 | −74.9 | + 85.0 |
|   |   |   | 1.25 | −24.1 | −38.8 | + 16.2 |
| 1 | —CH$_3$ | —COOC$_2$H$_5$ | 5 | −82.2 | −92.5 | +140.8 |
|   |   |   | 2.5 | −86.0 | −93.7 | +105.4 |
|   |   |   | 1.25 | −30.6 | −40.6 | + 11.4 |
| 1 | —CH$_3$ | —CH$_3$ | 5 | −84.8 | −92.7 | +108.2 |
|   |   |   | 2.5 | −66.8 | −78.8 | + 32.7 |
|   |   |   | 1.25 | −13.3 | −17.6 | + 16.2 |
| 2 | —CH$_3$ | —CH$_3$ | 5 | −46.3 | −51.1 | + 64.2 |
|   |   |   | 2.5 | −22.5 | −32.2 | + 42.3 |
|   |   |   | 1.25 | −10.6 | −12.4 | + 21.4 |

The local anesthetic properties of the compounds of the invention were evaluated by the Blink Response Test. Rabbits of both sexes which had been kept under standard diet condition and water ad libitum were topically treated in the eyeball with saline solutions or suspensions having the indicated concentration of the compound under investigation. Five minutes after treatment the animals were tested for their palpebral and corneal response (blinking). The results are shown in Table 4.

TABLE 4

BLINK RESPONSE

| n | R | COMPOUND I R' | No. of Animals Tested | Concentration % | No. of Animals Blinking |
|---|---|---|---|---|---|
| 1 | —H | —CH$_2$CH$_2$N(C$_2$H$_5$)(C$_2$H$_5$) | 5 | 5 | 0 |
| 1 | —H | —CH$_2$CH$_2$OH | 5 | 5 | 0 |
| 1 | —CH$_3$ | —CH$_3$ | 5 | 5 | 0 |
| 1 | —H | —CH(CH$_3$)(CH$_3$) | 5 | 5 | 0 |
| 1 | —CH$_2$CH$_2$OH | —CH$_2$CH$_2$OH | 5 | 3 | 3 |
| 1 | —CH$_3$ | —COOC$_2$H$_5$ | 5 | 3 | 0 |

The compounds of the invention may be administered topically in the form of salves, ointments, solutions, suspensions, etc., rectally in the form of suppositories, orally in the form of capsules, tablets, etc., or parenterally in the form of injectable solutions or suspensions.

In forming capsules, tablets, etc., the compounds may be admixed with conventional adjuvants such as starch, talcum, magnesium stearate, etc., and tabletted according to well-known methods.

Suppositories and suspensions for rectal and topical applications may be formed utilizing conventional and well-known compounding agents such as glycerine, polyethylene glycol, lavolin, etc.

The compounds may also be incorporated in Collyrium solutions for administration to the eye.

Injectable solutions can be prepared employing physiological saline solutions, etc.

For topical application, the ointment, salve, solution, etc., may contain from about 1 to about 5%, by weight, of the compound of the invention.

When administered orally, rectally, or parenterally, unitary dosages of the compounds of the invention for humans may range from about 5% to about 200 mg. Generally, the daily dosage may range from about 150 to about 600 mg. Obviously, the dosage in any individual application will depend upon the purpose for which the compound is administered.

I claim:

1. A compound of the formula:

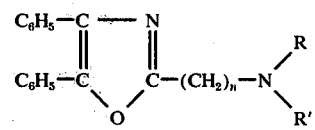

or a pharmaceutically acceptable salt thereof, wherein n is the integer 1 or 2 and R and R' are the same or different and represent hydrogen, alkyl of 1 to 4 carbon atoms, hydroxyalkyl of 1 to 4 carbon atoms, dialkylaminoalkyl wherein the alkyl is of 1 to 4 carbon atoms and carbalkoxy wherein the alkyl is of 1 to 4 carbon atoms.

2. 2-(N-methyl-N-carbethoxy)aminomethyl-4,5-diphenyloxazole, or a pharmaceutically acceptable salt thereof.

3. 2-(2-diethylaminoethyl)aminomethyl-4,5-diphenyloxazole, or a pharmaceutically acceptable salt thereof.

4. 2-dimethylaminomethyl-4,5-diphenyloxazole, or a pharmaceutically acceptable salt thereof.

5. 2-[bis(2-hydroxyethyl)]aminomethyl-4,5-diphenyloxazole, or a pharmaceutically acceptable salt thereof.

6. 2-dimethylaminoethyl-4,5-diphenyloxazole, or a pharmaceutically acceptable salt thereof.

* * * * *

UNITED STATES PATENT OFFICE
CERTIFICATE OF CORRECTION

Patent No. 4,020,082　　　　　　　　　Dated April 26, 1977

Inventor(s) ENZO MARCHETTI

It is certified that error appears in the above-identified patent and that said Letters Patent are hereby corrected as shown below:

On the title page insert:

--[73] Assignee: INSTITUTO FARMACOLOGICO SERONO, S.p.A., Rome, Italy - Via Casilina 125--

Signed and Sealed this

Eighteenth Day of October 1977

[SEAL]

Attest:

RUTH C. MASON
Attesting Officer

LUTRELLE F. PARKER
Acting Commissioner of Patents and Trademark